(12) United States Patent
Sagripanti et al.

(10) Patent No.: US 7,943,148 B1
(45) Date of Patent: May 17, 2011

(54) AMINO ACID SITES IN FLAVIVIRUS E PROTEINS USEFUL FOR DEVELOPMENT OF DIAGNOSTICS AND VACCINES

(75) Inventors: Jose-Luis Sagripanti, Bel Air, MD (US); Raja Mazumder, Reston, VA (US); Cathy Huey-Hwa Wu, Potomac, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/061,067

(22) Filed: Apr. 2, 2008

Related U.S. Application Data

(60) Provisional application No. 60/921,747, filed on Apr. 4, 2007.

(51) Int. Cl.
*A61K 39/12* (2006.01)
(52) U.S. Cl. ............... 424/218.1; 424/186.1; 435/5
(58) Field of Classification Search .......... None
See application file for complete search history.

(56) References Cited

U.S. PATENT DOCUMENTS 7,416,733 B2 * 8/2008 Garry et al. ............... 424/218.1
2004/0253578 A1 * 12/2004 Roberts et al. ............ 435/5

OTHER PUBLICATIONS

Wong et al. Detection of human anti-flavivirus antibodies with a west nile virus recombinant antigen microsphere immunoassay. J Clin Microbiol. Jan. 2004;42(1):65-72.*
Leyssen et al. Perspectives for the Treatment of Infections with Flaviviridae. J Clin Microbiol. Jan. 2000; 13(1): 67-87.*

* cited by examiner

*Primary Examiner* — Zachariah Lucas
*Assistant Examiner* — Michelle Horning
(74) *Attorney, Agent, or Firm* — Ulysses John Biffoni

(57) ABSTRACT

Highly immunoreactive viral peptides are disclosed which are derived from the E protein of major groups of the Flavivirus genus by computational analyses. These peptides are used in reliable diagnostic methods for the detection and diagnosis of Flavivirus, detecting the presence of antibodies against Flavivirus, and to form vaccine composition(s) for the prevention of Flavivirus infections in humans.

8 Claims, No Drawings

AMINO ACID SITES IN FLAVIVIRUS E PROTEINS USEFUL FOR DEVELOPMENT OF DIAGNOSTICS AND VACCINES

RELATED APPLICATION

This Application claims the benefit of priority from U.S. Provisional Application Ser. No. 60/921,747 filed on Apr. 4, 2007.

FIELD OF THE INVENTION

The present invention relates to conserved and highly immunoreactive viral peptides of Flavivirus cloned from the genome of mosquito-borne Flaviviruses such as Dengue virus, Yellow Fever Virus, West Nile virus, Saint Louis Encephalitis virus, or Japanese encephalitis virus and Tick Borne Flaviviruses as Tick-borne encephalitis virus, Omsk Hemorrhagic Fever virus, or Louping ill virus, Flaviviruses with unknown vector like Modoc virus, Apoi Virus, or Rio Bravo virus, and its utilization in the development of reliable diagnostic methods for the detection and diagnosis of Flavivirus, as well as its use in a vaccine composition for the prevention of Flavivirus infections in humans.

BACKGROUND OF THE INVENTION

Positive-sense single-stranded RNA (+ssRNA) viruses include highly virulent human pathogens. Within the Flaviviridae family, the genus Flavivirus comprises more than 70 +ssRNA viruses [1], including mosquito-borne Flaviviruses such as Dengue Virus, Yellow Fever Virus, West Nile Virus, Saint Louis Encephalitis Virus, or Japanese Encephalitis Virus and Tick Borne Flaviviruses as Tick-borne encephalitis virus, Omsk Hemorrhagic Fever virus, or Louping ill virus, Flaviviruses with unknown vector like Modoc Virus, Apoi Virus, or Rio Bravo Virus. Dengue virus (DENV), in particular, is an acute viral disease transmitted by mosquito, and one of the most widespread vector-borne viral diseases in humans. Dengue is caused by any of four antigenically distinct serotypes: dengue-1 (DENV1), dengue-2 (DENV2), dengue-3 (DENV3), and dengue-4 (DENV4). There are an estimated 50-100 million cases of dengue fever annually worldwide, half a million of which result in severe forms of the disease, dengue hemorrhagic fever and dengue shock syndrome [2]. Generally, infection with one serotype confers future protective immunity against that particular serotype, but not against the others. In fact, dengue hemorrhagic fever may occur from sequential infection by different virus serotypes in a process called antibody-mediated disease enhancement, where antibodies raised against the first serotype enhance infection with the second serotype [3].

The major envelope glycoprotein (referred to as E protein hereafter) of DENV and of other flaviviruses is responsible for important phenotypic and immunogenic properties of the virion and is believed to lead the virus entry into cells [4,5]. The E protein mediates virus assembly and virus-cell membrane fusion, and initiates infection through binding to cell surfaces. This protein is the principal component of the external surface of the DENV virion and represents the dominant virus antigen, evoking protective immune responses. Dengue serotypes can be distinguished by virus-neutralizing antibodies, but non-neutralizing antibodies against the E protein are cross-reactive. These non-neutralizing antibodies may help bring the virion into close proximity to the normal virus receptor, thus enhancing virus binding and increasing the number of infected cells, with concomitant exacerbation of the disease [6].

While it is well established that the E protein is one of the major proteins responsible for the pathogenicity and immunogenic properties of flaviviruses, the exact residues/regions responsible for these traits remain to be identified. Single-residue substitutions mapped to different parts of the E protein were reported to cause flavivirus attenuation [7], implying that several residues within the E protein are responsible for phenotypic and pathogenic properties. The crystal structure of the soluble ectodomain of DENV2 E protein reveals a hydrophobic pocket lined by residues that influence the pH threshold for membrane fusion [8-10]. The protein has three structural domains (DI, DII, DIII) that map closely to the three antigenic regions (C, A, and B, respectively) [4]. DENV enters the host cell when the E protein binds to a yet undefined cell receptor and responds to a reduced pH of the endosome by a conformational change [1,1]. This conformational change induces fusion of the virus and the host cell membrane. The crystal structure of DENV3 E protein indicates that the serotype-specific mutations that allow viral evasion from immune surveillance (neutralization escape mutations) are all located on the surface of domain III, which has been implicated in receptor binding [12, 13]. The apparent involvement of the host immune system in disease pathogenesis, the so-called antibody-dependent enhancement (ADE), has hampered development of a vaccine against dengue. Therefore it is important to identify specific regions of the E protein having a high potential success as targets in order to develop robust diagnostics and vaccines against Flavivirus, specifically dengue virus.

SUMMARY OF THE INVENTION

Accordingly, it is an object of the present invention to identify those peptides of the flavivirus E protein that are highly antigenic by using several complementary bioinformatics methods to analyze sequence conservation, selection pressure, immunogenic properties and structural features of the Flavivirus E protein.

One embodiment of the present invention is a purified and isolated peptide selected from the group of amino acid sequences consisting of SEQ ID NO:1 through SEQ ID NO:16. Another embodiment of the present invention is a recombinant fusion protein comprising a heterologous amino acid sequence fused to an isolated peptide selected from the group of amino acid sequences consisting of SEQ ID NO:1 through SEQ ID NO:16. It is preferred that the heterologous amino acid sequence codes for glutathione S-transferase.

Another embodiment of the present invention is a method for producing a purified antibody against one or more isolated peptide(s) selected from the group of amino acid sequences consisting of SEQ ID NO:1 through SEQ ID NO:16, comprising injecting into a non-human mammalian host, an immunologically effective amount of the isolated peptide, and isolating and purifying the antibody produced.

Another embodiment of the present invention is a vaccine composition for immunizing an individual against infection from one or more flaviviruses comprising one or more isolated peptide(s) of claim 1, and a pharmacologically acceptable carrier. Another embodiment of the present invention is a method for immunizing an individual against infection from one or more flaviviruses, which comprises steps of administration of the vaccine composition described above into a subject in need.

Yet another embodiment of the present invention includes a method for determining the presence or absence of flavivirus antibodies in a biological test sample, comprising: providing one or more purified and isolated peptide(s) selected from the group of amino acid sequences consisting of SEQ ID NO:1 through SEQ ID NO:16; contacting the biological test sample suspected of containing flavivirus antibodies with said isolated peptide; incubating the resultant mixture under conditions sufficient to allow the formation of an immunological (antibody-antigen) complex; and examining the mixture for the presence of such an immunological complex, whereby the formation of the complex indicates the presence of flavivirus antibodies in the test sample. It is preferred that the biological test sample is human blood, serum, plasma or spinal fluid and that the presence of the immunological complex is determined following incubation with an indicator reagent under conditions permitting a reaction to occur. It is also preferred that the indicator reagent is a mammalian anti-human immunoglobulin attached to an enzyme which reacts with a substrate to form a colored product.

Another embodiment of the present invention is a diagnostic test kit for the detection of antibodies to a flavivirus, comprising: one or more purified and isolated peptide(s) selected from the group of amino acid sequences consisting of SEQ ID NO: 1 through SEQ ID NO:16; and an indicator reagent capable of detecting an immunological (antigen antibody) complex which contains said isolated peptide. It is preferred that one or more control standards and a specimen diluent and/or washing buffer be included in said kit. It is also preferred that the isolated peptide of the kit is immobilized to a solid support, such as the well of a titration microplate.

Another embodiment of the present invention includes a diagnostic test kit for the detection of antibodies to flavivirus, comprising: a purified and isolated peptide, selected from the group of amino acid sequences consisting of SEQ ID NO:1 through SEQ ID NO:16; an indicator reagent capable of detecting an immunological (antigen-antibody) complex which contains the one or more isolated peptides, and at least one of the following: (a) a solid support immobilizing the isolated peptide; and (b) a well of a titration microplate containing the isolated peptide.

Another embodiment of the present invention includes a purified and isolated peptide selected from the group of amino acid sequences consisting of SEQ ID NO:1 through SEQ ID NO:10.

Another embodiment of the present invention is a method for producing a purified antibody against one or more isolated peptide(s) selected from the group of amino acid sequences consisting of SEQ ID NO:1 through SEQ ID NO:10, comprising injecting into a non-human mammalian host, an immunologically effective amount of the isolated peptide, and isolating and purifying the antibody produced.

Another embodiment of the present invention is a vaccine composition for immunizing an individual against infection from Dengue virus comprising one or more isolated peptide selected from the group of amino acid sequences consisting of SEQ ID NO:1 through SEQ ID NO:10, and a pharmacologically acceptable carrier. Another method of the present invention is a method for immunizing an individual against infection from one or more Dengue viruses, which comprises steps of administration of this vaccine composition into a subject in need.

Another embodiment of the present invention includes a method for determining the presence or absence of dengue virus antibodies in a biological test sample, comprising: providing one or more purified and isolated peptide(s) selected from the group of amino acid sequences consisting of SEQ ID NO: 1 through SEQ ID NO:10; contacting the biological test sample suspected of containing flavivirus antibodies with said isolated peptide; incubating the resultant mixture under conditions sufficient to allow the formation of an immunological (antibody-antigen) complex; and examining the mixture for the presence of such an immunological complex, whereby the formation of the complex indicates the presence of Dengue virus antibodies in the test sample. It is preferred that the biological test sample is human blood, serum or plasma and that the presence of the immunological complex is determined following incubation with an indicator reagent under conditions permitting a reaction to occur. It is also preferred that the indicator reagent is a mammalian anti-human immunoglobulin attached to an enzyme which reacts with a substrate to form a colored product.

Another embodiment of the present invention is a diagnostic test kit for the detection of antibodies to a Dengue virus, comprising: one or more purified and isolated peptide(s) selected from the group of amino acid sequences consisting of SEQ ID NO: 1 through SEQ ID NO:10; and an indicator reagent capable of detecting an immunological (antigen antibody) complex which contains said isolated peptide selected from the group of amino acid sequences consisting of SEQ ID NO:1 through SEQ ID NO:10. It is preferred that the diagnostic test further comprises one or more control standards and a specimen diluent and/or washing buffer. It is also preferred that the diagnostic test kit contains one or more isolated peptide (s) that is immobilized to a solid support, wherein the solid support is a titration microplate.

Another embodiment of the present invention is a diagnostic test kit for the detection of antibodies to Dengue virus, comprising: one or more purified and isolated peptide(s), selected from the group of amino acid sequences consisting of SEQ ID NO:1 through SEQ ID NO:10; an indicator reagent capable of detecting an immunological (antigen-antibody) complex which contains said one or more isolated peptide(s), and at least one of the following: a) a solid support immobilizing one or more of these isolated peptide(s); and b) a well of a titration microplate containing one or more of these isolated peptide(s) selected from the group of amino acid sequences consisting of SEQ ID NO:1 through SEQ ID NO:10.

Another object of the invention is to provide an improved and more reliable diagnostic method for determining current and past infection of Flavivirus through the detection of IgM and IgG antibodies in a clinical or biological test sample, which incorporates one or more peptide selected from the group consisting of SEQ ID NO:1 through SEQ ID NO:16 as an immunoreagent due to its high specificity and sensitivity of binding to flavivirus antibodies.

Still another object of the present invention is to provide an improved and more reliable diagnostic method for monitoring and detecting flavivirus, specifically Dengue virus, in public health and environmental studies using antibodies specifically raised against one or more of the peptides selected from the group consisting of SEQ ID NO:1 through SEQ ID NO:16 that can effectively capture, isolate and concentrate Flavivirus particles in a test sample, and which avoids disadvantages associated with the use of other conventional methods.

Yet another object of the invention is to provide a vaccine composition which comprises one or more of the peptides selected from the group consisting of SEQ ID NO:1 through SEQ ID NO:16, and its use thereof, for the immunization and prevention of Flavivirus, including mosquito-borne Flaviviruses as a Dengue virus, Yellow Fever Virus, West Nile virus, Saint Louis Encephalitis virus, or Japanese encephalitis virus and Tick Borne Flaviviruses as Tick-borne encephalitis virus, Omsk Hemorrhagic Fever virus, or Louping ill virus, Flaviviruses with unknown vector like Modoc virus, Apoi Virus, or Rio Bravo virus, and more specifically Dengue virus.

According to the present invention there is provided a highly immunoreactive viral peptide, selected from the group consisting of SEQ ID NO:1 through SEQ ID NO:16.

In accordance with the present invention, any nucleic acid sequence which encodes the amino acid sequence of a peptide selected from the group consisting of SEQ ID NO:1 through SEQ ID NO:16, can be used to generate recombinant molecules which express one or more of these peptides. Methods for making such derivatives may be readily accomplished by one of ordinary skill in the art (59).

It is well established that the information for determining the three-dimensional structure of a polypeptide is carried entirely within its amino acid sequence. Moreover, portions of the sequence comprising amino acids that define specific conformational epitopes can be widely dispersed with intervening sequences along the length of the molecule. Based on the predicted tertiary (and quarternary) structure of the polypeptide, the three-dimensional coordinates of the conformational epitopes are eventually brought into their correct configuration due to the three-dimensional folding of the polypeptide's primary structure. Accordingly, it is expected that the amino acid sequence can be subject to a certain degree of modification based on the higher level of structural organization of the polypeptide which will not alter the conformational structure and immunochemical reactivity of the epitope substantially. Therefore, segments of the polypeptide located between groups of residues defining the various epitopes may not critically alter the presentation of the epitope following extension, deletion, insertion, or substitution of residues within these intervening sequences. The epitopes of the present invention include the peptides selected from the group consisting of SEQ ID NO:1 through SEQ ID NO:16.

Moreover, depending on the chemical properties of the amino acid residues contained within a sequence which defines a particular epitope, substitutions with residues having similar functional groups may not alter the immunochemical reactivity of the epitope. In this regard, it is expected that as long as the immunochemical reactivity of a peptide selected from the group consisting of SEQ ID NO:1 through SEQ ID NO:16 is preserved so that it remains recognizable by anti-flavivirus antibodies, preferably anti-dengue virus antibodies, various amino acid residues in the amino acid sequence may be deleted, inserted or substituted by other amino acid residues, to generate derivatives. This is providing, of course, that the particular change incorporated provides an advantage in its use, such as in dealing with strain-to-strain variations among different isolates of Flavivirus. Furthermore, amino acid substitutions which are contemplated within the scope of the invention are those in which the chemical nature of the substitute residue is similar to that of the original amino acid. Amino acids are generally considered to possess similar chemical properties based on their functional group and therefore, include combinations such as: Gly/Ala; Asp/Glu; Asn/Gln; Val/Ile/Leu; Ser/Thr; Lys/Arg; and Phe/Tyr. These derivatives of a peptide selected from the group consisting of SEQ ID NO:1 through SEQ ID NO:16 may therefore comprise extensions, substitutions, insertions and/or deletions of the amino acid sequences, providing their immunochemical reactivity to Flavivirus, preferably Dengue virus antibodies is preserved. Two peptides are said to have equivalent immunochemical reactivity and within the scope of this invention when they are capable of being recognized by the same antibodies raised against one of the peptides selected from the group consisting of SEQ ID NO:1 through SEQ ID NO:16.

A peptide selected from SEQ ID NO:1 through SEQ ID NO:16 of the present invention can be generated by methods known in the art that provide the conformational epitopes of interest, including chemical synthetic methods and recombinant DNA technology. A preferred method of preparing a peptide of the present invention is through recombinant DNA expression in a host cell followed by isolation and purification of the peptide. In accordance with the present invention, nucleic acid sequences which encode a peptide selected from SEQ ID NO:1 through SEQ ID NO:16, fragments of the peptide, fusion proteins or functional equivalents thereof, may be used in recombinant DNA molecules that direct the expression of the peptide in appropriate host cells. In order to express an immunologically active peptide of the present invention, the nucleotide sequence encoding the peptide selected from SEQ ID NO:1 through SEQ ID NO: 16, or its functional equivalent, is inserted into an appropriate expression vector which contains the necessary elements for the transcription and translation of the inserted coding sequence. Depending on the host cell selected, the expression vector will normally contain control elements of DNA that effect expression of the DNA sequence and usually include a promoter, ribosome binding site, translational start and stop sites, and a transcriptional termination site.

Therefore, according to yet another aspect of the present invention, there is provided a method for preparing a peptide of the present invention which comprises isolating the cDNA sequence corresponding to the peptide, inserting the cDNA sequence into an expression vector such that it is capable of being expressed in an appropriate host cell, transforming the host cell with the expression vector, culturing the transformed host cell, and isolating and purifying a peptide selected from SEQ ID NO:1 through SEQ ID NO:16.

Methods which are well known to those skilled in the art can be used to construct expression vectors containing the nucleic acid sequences corresponding to a peptide of the present invention and appropriate transcriptional or translational controls. The desired cDNA sequence obtained as described above may be inserted into an expression vector using known and standard techniques [59]. The expression vector is normally cut using restriction enzymes and the cDNA sequence is inserted using blunt-end or staggered-end ligation. The cut is usually made at a restriction site in a convenient position in the expression vector such that, once inserted, the cDNA sequences are under the control of the functional elements of cDNA that effect its expression. Transformation and culturing of a host cell and isolation of the peptide as required may also be carried out using standard techniques.

In bacterial systems, a number of expression vectors may be selected depending upon the use intended for the peptide or protein to be expressed. For example, when large quantities of a peptide or protein are needed for the production of antibodies, vectors which direct high level expression of fusion proteins that are readily purified may be desired. According to a related aspect of the present invention, there is provided an expression vector containing the nucleic acid sequence which codes for a peptide of the present invention and which vector is capable of expressing the nucleic acid sequence. The expression vector is suitable for expression in a bacterial system, preferably E. coli, and includes, but is not limited to the multifunctional E. coli cloning and expression vector pGEX (PROMEGA Corporation, Madison, Wis. 53711). In this particular vector, the peptide coding sequence is ligated, at its 5'-end, into the vector in frame with the heterologous sequence for the glutathione S-transferase (GST), at its 3'-end, and the resulting hybrid polynucleotide sequence expressed as a fusion protein. In general, such fusion proteins are soluble and can easily be purified from lysed cells by adsorption to glutathione-agarose beads followed by elution in the presence of free glutathione. Proteins made in such systems are designed to include cleavage sites so that the cloned peptide of interest can be released from the GST moiety by adding the appropriate protease, such as thrombin.

Therefore, according to a preferred embodiment of the present invention, there is provided a plasmid that expresses the fusion protein, GE2, comprising a peptide of the present invention, which is fused to the glutathione-S-transferase (GST) polypeptide. The nucleic acid sequence corresponding to the peptide, represented by SEQ ID NO:1, is inserted into a pGEX.sub.20 expression vector such that the open reading frame of the peptide nucleotide sequence is in frame with the GST open reading frame 1.

The vector expressing the peptides of the present invention was produced by incorporating sequences derived from cDNA from the DENV-2 genome. The proof reading DNA polymerase "Phusion" (FINNZYMES, Inc. Woburn, Mass. 01801) was used with the full length DENV-2 cDNA as template. E-protein cDNA corresponding to the peptides of the present invention were amplified by PCR and cloned into expression vectors. Alternatives to starting material, viruses, protein or nucleic acid synthesis sequence amplification, cloning, and/or expression, can be utilized without departing from the spirit of this invention.

The peptides provided herein may be employed as an immunoreagent in diagnostic assays used to screen biological test samples for the presence of Flavivirus, specifically Dengue virus, antibodies and therefore, aid the practitioner or clinician in the detection and diagnosis of Flavivirus infection. Accordingly, the present invention provides methods for immunochemically detecting anti-Flavivirus antibodies in a biological test sample using one or more peptide(s) of the present invention. Essentially, any immunoassay format which is designed to utilize one or more peptide(s) of the present invention as a capture antigen for detecting anti-Flavivirus antibodies may be employed. Methods for performing immunoassays are well known in the art and the present invention is not intended to be limited to any particular immunoassay. Both homogeneous and heterogeneous immunoassays may be used.

In general, a biological test sample suspected of containing Flavivirus antibodies is contacted and incubated with one or more peptide(s) of the present invention for a time and under conditions which allow a reaction to occur. Preferably, one or more peptide(s) of the present invention is attached to a suitable solid support. If Flavivirus antibodies are present in the test sample, they will form an immunological complex (antigen-antibody complex) with one or more peptide(s) of the present invention and become attached to the solid support. As an option, the solid support may be washed with a buffer solution to remove any unbound components which in certain instances, will help to improve the sensitivity of the assay. After washing, the immunological complex is reacted with an indicator reagent and allowed to incubate for a time and under conditions for a second complex to form. Immunological complexes are detected by any of a number of known techniques, depending on the format of the assay. For example, a conjugate of an anti-mammalian immunoglobulin complexed with a label or signal-generating component (e.g. an enzyme) is commonly employed as an indicator reagent. The presence of an immunological complex confirms the presence of antibodies to a Flavivirus in the test sample and is determined by measuring the signal generated. As with many indicator reagents, the amount of antibody present is usually proportional to the signal generated. The presence of the immunological complex in the test sample may be detected visually or mechanically using, for example, an automated scanning and interpretation device.

A suitable solid support will depend upon the type of immunoassay format that is performed, however, it is desired that the type of support chosen will have reasonable strength and not interfere with the immunoreactivity of the immunological complex, nor the production of a detectable signal from the signal-generating component. Examples of solid supports include the walls of microwells of a reaction tray, test tubes, sheets, plates, slides, beads (e.g. polystyrene or glass), nitrocellulose strips, membranes, microparticles such as latex particles, chips of glass, plastic, and others.

The label or signal-generating component used as a means to detect the formation of an immunological complex will allow visual detection of a precipitate or a color change, visual detection by microscopy, or automated detection by spectrometry, radiometric measurement, or the like. Examples of signal-generating components include colloidal gold, fluorescent compounds, luminescent compounds, a chromogen, radioactive elements, enzymes (e.g. alkaline phosphatase, horseradish peroxidase and beta-galactosidase) and enhancer compounds (e.g. biotin, anti-biotin and avidin).

Accordingly, another aspect of the present invention provides a method for the diagnosis or detection of Flavivirus antibodies present in a biological test sample comprising the following steps: providing one or more peptide(s) of the present invention characterized in that the one or more peptide(s) is preferably immobilized onto a solid support; contacting and incubating the one or more peptide(s) with a biological test sample under conditions which allow the formation of an immunological (antigen-antibody) complex between the one or more peptide(s) and anti-Flavivirus antibodies; possibly removing unbound components from the resultant mixture; incubating the resultant mixture with an indicator reagent; and examining the mixture for the presence of the immunological complex, whereby the formation of the immunological complex indicates the presence of antibodies to Flavivirus in the test sample.

Generating Anti-Peptide Antibodies

It is further described that antibodies specifically reactive against one or more peptide(s) of the present invention can be generated through techniques well known in the art. Since the conformational antigenic determinants of a peptide of the present invention mimic similar structural features of the E protein, a peptide of the present invention is useful for the production of both polyclonal and monoclonal antibodies. Moreover, these antibodies, or fragments thereof, directed against one or more peptide(s) of the present invention are particularly useful in the development of diagnostics tests as valuable immunoreagents for determining Flavivirus infection through isolation and screening of viral particles and/or antigen. Thus, anti-peptide antibodies can be used in a number of clinical diagnostic procedures including conventional immunoassay formats to detect the presence of Flavivirus antigen in biological samples and immune capture formats in which small samples of Flavivirus particles can be isolated and concentrated. [60].

If polyclonal antibodies against one or more peptide(s) of the present invention are desired, a selected non-human mammalian host (e.g., mouse, rat, sheep, rabbit, goat, etc.) is injected with the peptide, optionally coupled to a carrier, to promote an immune response and the antibody thus produced is subsequently recovered and purified. According to preferred embodiment of the present invention, the mammalian host is immunized with the GE2 polypeptide as described above bearing one or more Flavivirus epitope(s), that is peptides selected from SEQ ID NO: 1 through SEQ ID NO: 16. The GE2 polypeptide is administered in the form of an injectable formulation whereby the GE2 polypeptide is admixed with a physiologically acceptable diluent. Adjuvants, such as Freund's complete or incomplete adjuvant, may be included in the formulation. The formulation is injected into the host over a suitable period of time, plasma samples being taken at appropriate intervals to assay for Flavivirus antibody. When an appropriate level of activity is obtained, the host is bled. Antibody is then recovered and purified from the blood plasma using standard procedures, for example, by immunoaffinity chromatography.

Although the polyclonal antibodies of the invention are preferred, a system containing various monoclonal antibodies functioning as a polyclonal system is also within the scope of the present invention. Monoclonal antibodies directed against Flavivirus conformational epitopes can also be readily produced using the GE2 polypeptide of the present invention by one skilled in the art. The general methodology for producing monoclonal antibodies using immortal antibody-producing cell lines, commonly known as hybridomas, is well known. Hybridomas can be created by the fusion of cells which produce anti-peptide antibody and an immortalizing cell which imparts long-term tissue culture stability to the hybrid cell. In the formation of the hybrid cell line, the first fusion partner, the antibody-producing cell, can be a spleen cell of a non-human mammalian host, such as a mouse or rat, which is innoculated with the GE2 polypeptide. After sufficient time has elapsed for the host to mount an antibody response, the antibody-producing cells are removed. Cells of an immortalizing cell line, such as a mouse or rat myeloma cell line, are fused with the antibody-producing cells and the resulting fusions screened to identify a cell line, such as a hybridoma, that secretes the desired monoclonal antibody. The fusion of an antibody-producing cell with an immortal cell can be accomplished by standard procedures [61, 62]. The fused cell line may be cultured and the monoclonal antibody screened and purified for the production of anti-peptide antibody from the culture media in a similar manner to recovering polyclonal antibody.

Therefore, according to a further aspect of the present invention, there is provided a method for producing a purified antibody against Flavivirus antigen, wherein an effective amount of a one or more peptide(s) of the present invention, having an amino acid sequence represented by SEQ ID NO:1 through SEQ ID NO:16, is injected into a non-human mammalian host, and collecting the antibody produced.

Monoclonal or polyclonal antibodies that have been raised or developed using the one or more peptide (s) of the present invention can be used in an immunoassay as a capture reagent to detect the presence of Flavivirus capsid protein, or viral particle, in a biological test sample. Essentially, any immunoassay format which is designed to utilize the anti-peptide antibody as a capture reagent may be employed. Methods for performing immunoassays are well known in the art and the present invention is not intended to be limited to any particular immunoassay.

In general, since the conformational antigenic determinants of one or more peptide (s) of the present invention mimic similar structural features of the E protein, anti-peptide antibodies may be employed in immune capture methods to isolate and concentrate Flavivirus particles which can subsequently be detected by extracting viral RNA and applying reverse transcriptase polymerase chain reaction (RT-PCR). According to a preferred embodiment of the invention, an immune capture method is provided for the purpose of isolating and concentrating Flavivirus particles whereby polystyrene paddles, or other suitable solid absorbent materials, are coated with antisera raised against one or more peptide(s) of the present invention. This method is highly effective in detecting small amounts of the virus in a test sample which is determined by extraction of viral RNA and applying RT-PCR thereon, preferably a nested polymerase chain reaction.

A suitable solid support or absorbent material will depend upon the type of immunoassay format that is performed, however, it is desired that the type of support chosen will have reasonable strength and not interfere with the immunoreactivity of the immunological complex. Examples of solid supports include the walls of microwells of a reaction tray, test tubes, sheets, plates, slides, beads (e.g. polystyrene or glass), nitrocellulose strips, membranes, microparticles such as latex particles, chips of glass, plastic, and others.

Accordingly, another aspect of the present invention provides a method for the detection of Flavivirus particles (i.e. analyte) in a biological test sample, comprising the following steps: providing a purified antibody raised against one or more peptide(s) of the present invention selected from SEQ ID NO:1 through SEQ ID NO:16, or a homologous sequence, fragment, or analog thereof, characterized in that the anti-peptide antibody is preferably immobilized onto a solid support; contacting and incubating the anti-peptide antibody with a biological test sample under conditions which allow the formation of a complex between the anti-peptide antibody and any Flavivirus analyte which may be present in the test sample; possibly removing unbound components from the resultant mixture; and examining the mixture for the presence of Flavivirus analyte.

Diagnostic Test Kits

The novel Flavivirus peptide(s), selected from SEQ ID NO:1 through SEQ ID NO:16, described herein will typically be packaged in the form of a diagnostic kit for use in the detection and diagnosis of Flavivirus infection. The kit will normally contain, in a separate container, one or more peptide(s) of the present invention or the anti-peptide antibody (of the present invention) as the immunoreagent. Moreover, depending on the immunoreagent employed and the type of Flavivirus analyte to be detected, the kit may additionally contain positive and negative control samples, an indicator reagent, such as a labeled anti-human antibody and a signal generating reagent (e.g. enzyme substrate in the case of an enzyme label) if the label does not generate a signal directly. As described herein, the term "separate container" refers to any material capable of holding within fixed limits the one or more peptide(s) of the present invention or the anti-peptide antibody of the present invention, as well as other components provided in the diagnostic test kit, such as strips in immunochromatography kits (indicated below). Instructions for carrying out the assay will normally be included in the kit. Such instructions generally describe the immunoreagent concentration or at least one assay method parameter such as the relative amounts of immunoreagent and sample to be admixed, time periods for immunoreagent/sample admixtures, temperature, buffer conditions and the like.

If desired, the one or more peptide or anti-peptide antibody of the present invention can be typically immobilized to a solid support material by passive adsorption or through covalent linkage in which there are many techniques available that are well known to those skilled in the art. Solid supports advantageous for immobilizing the one or more peptide or anti-peptide antibody of the present invention are also well known to those skilled in the art. A suitable support will depend upon the type of immunoassay format that is performed, however, it is desired that the type of support chosen will have reasonable strength and not interfere with the immunoreactivity of the immunological complex, nor the production of a detectable signal from the signal-generating component. Examples of solid supports include the walls of microwells of a reaction tray, test tubes, sheets, plates, slides, beads (e.g. polystyrene or glass), nitrocellulose strips, membranes, microparticles such as latex particles, chips of glass, plastic, and others.

The indicator reagent should comprise a label or signal-generating component capable of indicating the formation of an immunological complex by the immunoreagent of the present invention and the captured Flavivirus analyte. The indicator reagent of the diagnostic test kit can be provided in solution, as a liquid dispersion or as a substantially dry power, e.g. in a lyophilized form. Where the indicator reagent utilizes an enzyme as the signal-generating component, the enzyme's substrate can also be provided in a separate container of the diagnostic test kit. Moreover, the label or signal-generating component used as a means to detect the formation of an immunological complex through antigen-antibody binding will allow visual detection of a precipitate or a color change, visual detection by microscopy, or automated detection by spectrometry, radiometric measurement, or the like. Examples of signal-generating components include colloidal gold, fluorescent compounds (e.g. fluorescein and rhodamine), luminescent compounds, a chromogen, radioactive elements, enzymes (e.g. alkaline phosphatase, horseradish peroxidase and beta-galactosidase) and enhancer compounds (e.g. biotin, anti-biotin and avidin).

As an example of a kit for detecting Flavivirus antibody, a predetermined amount of one or more peptide of the present invention selected from SEQ ID NO:1 through SEQ ID NO:16 can be immobilized to a microwell of a reaction tray so that it is capable of immunologically binding to incoming Flavivirus antibody. The indicator reagent can be a labeled mammalian anti-human antibody which will recognize and bind to any Flavivirus antibody that may be present in the test sample. The labeled mammalian anti-human antibody can utilize an enzyme as the signal-generating component, and the enzyme's substrate additionally provided if the enzyme does not generate a signal directly.

Some candidate vaccines being currently developed are recombinant peptides of the major structural protein expressed in eukaryotes [63]. Advantages to using recombinant peptides in vaccine formulations compared to attenuated viruses are that peptides can be more efficiently produced and conveniently purified. Furthermore, there is no possibility that the resulting vaccine will contain any live intact virus particles, thereby avoiding a risk of infectivity.

Therefore, according to yet another aspect of the present invention, there is provided a vaccine composition comprising one or more peptide of the present invention selected from SEQ ID NO:1 through SEQ ID NO:16, or a homologous sequence, fragment, or analog thereof, and a pharmaceutically acceptable carrier, which protects mammals against challenge with Flavivirus following immunization.

Moreover, a use of the vaccine for immunizing a individual against infection against Flavivirus, wherein the vaccine comprises an immunologically effective amount of one or more peptide selected from SEQ ID NO:1 through SEQ ID NO:16, in combination with a pharmacologically acceptable carrier, is also provided. Pharmacologically acceptable carriers are well known to those of ordinary skill in the art [64]. They include liquid media suitable for use as vehicles to introduce the peptide into a patient but should not in themselves induce the production of antibodies harmful to the individual receiving the composition. An example of such liquid media is saline solution. Moreover, the vaccine formulation may also contain an adjuvant for stimulating the immune response and thereby enhancing the effect of the vaccine.

An "immunologically effective amount" means that the administration of that amount to a subject, either in a single dose or as part of a series, is effective for treatment, as defined above. This amount varies depending upon the health and physical condition of the subject to be treated, the species of the subject to be treated (e.g. non-human mammal, primate, etc.), the capacity of the subject's immune system to synthesize antibodies, the degree of protection desired, the formulation of the vaccine, the strain of infecting Flavivirus, and other relevant factors. It is expected that the amount will fall in a relatively broad range that can be determined through routine trials.

Vaccines of the present invention may be administered by any convenient method for the administration of vaccines including oral, intranasal/inhalation, and parenteral (e.g. intravenous, subcutaneous or intramuscular) injection. The treatment may consist of a single dose of vaccine or a plurality of doses over a period of time.

These and other advantages and features of novelty which characterize the invention are pointed out with particularity in the claims annexed hereto and forming a part hereof. For a better understanding of the invention, its advantages, and objects obtained by its use, reference may be made to the accompanying descriptive matter in which there is illustrated and described preferred embodiments of the invention. In addition, incorporated references and their figures are cited in brackets.

DETAILED DESCRIPTION OF THE INVENTION

Analysis of Sequence Conservation in the Flavivirus Genus and Dengue Species

Sequence conservation of E proteins was analyzed based on structure-guided multiple sequence alignment, neighbor-joining phylogenetic tree, and Shannon entropy. Twelve E proteins representative sequences were chosen from the major flavivirus groups where the genome polyproteins are available [65 including FIG. 1]. Conserved residues involved in critical interactions have also been identified [65 including FIG. 1]. The taxonomic groups were defined based on the ICTVdB nomenclature of the International Committee on Taxonomy of Viruses [1].

The E protein sequences were extracted from polyproteins in the UniProt Knowledgebase (UniProtKB) [1,4]. The multiple sequence alignment was manually edited using the Cn3D sequence-structure viewer [1,5], guided by a reference structure alignment in MMDB [6] using three E protein structures (1OKE, 1UZG, 1SVB), which were originally deposited in PDB [1,6]. The manual editing involves superimposing and aligning the structures in the structure viewer and then adding individual sequences manually and aligning them with the sequences from the structure. For the C-terminal regions outside the structural alignment (~100 aa), the sequences were aligned using ClustalW [1,7] and then manually verified. A phylogenetic tree was generated using the neighbor-joining program in ClustalW with 1,000 bootstrap replicates. The bootstrap values indicate the confidence in the estimated tree branches. The sequence conservation of dengue E proteins was further analyzed based on the multiple sequence alignment of 740 full-length proteins from all four serotypes. The conservation in each amino acid position was quantified based on the Shannon entropy, as estimated by the nine component Dirichlet mixture algorithm [1,8]. The entropy calculation took into account conservative substitutions of amino acids with similar physicochemical properties.

Evolutionary Selection Analysis of Dengue Serotypes

Selection analysis was studied using maximum likelihood methods to calculate non-synonymous/synonymous (dN/dS) nucleotide substitution ratio based on codon alignment and phylogenetic tree. The maximum likelihood methods evaluate the probability that the chosen model has produced the observed data. DNA sequences were extracted from the NCBI nucleotide nt database [19], resulting in four datasets consisting of 146, 269, 121, and 204 sequences for DENV1, DENV2, DENV3, and DENV4, respectively, as well as a fifth dataset totaling 740 sequences with all four serotypes combined. The codon alignment and consensus neighbor-joining tree was derived using MEGA [20]. To quantify selective pressure at a given codon site, estimates of synonymous (dS) and non-synonymous (dN) substitution rates were compared using a statistical test as described earlier [21]. If dS>dN (or, dS<dN), then a site was inferred to be negatively (or positively) selected. We employed two likelihood based methods—Single Likelihood Ancestor Counting (SLAC) and Fixed Effects Likelihood (FEL) [22] and considered sites to be "selected" when both SLAC and FEL methods yielded a P-value of <0.01. SLAC reconstructs the most likely unobserved ancestral sequences, counts the number of non-synonymous and synonymous changes at every site, and tests whether the number of non-synonymous changes per non synonymous site is significantly different from the number of synonymous changes per synonymous site. FEL derives the branch lengths and substitution rate bias (global) parameters from the entire alignment, and then directly estimates the ratio of non-synonymous to synonymous rates under a codon-substitution model for each site in a sequence alignment holding all global parameters fixed. The FEL method is in general more powerful but also more computationally demanding than the SLAC method [22]. For this study we reported only those sites, which were concordantly classified with both methods. For the large combined set with all four serotypes, a more stringent cutoff of P<10-5 was used [22]. Selection analyses were performed using the HyPhy program [23], which took into account nucleotide substitution biases and dS and dN rate variation across sites. To exclude the possibility of erroneous selection inference due to recombination between different DENV serotypes, a maximum likelihood test for phylogenetic incongruence [24] was run to screen for possible recombination in the E protein; no statistically significant recombination breakpoints were identified in any of the DENV datasets.

Prediction of T-Cell Epitopes

Three online prediction programs, NetMHC 2.1 [25], MHCPred 2.0 [26] and RANKPEP [27], were used to analyze the four serotypes of dengue E proteins. As both MHC-I and -II molecules are highly polymorphic and the specificity of the alleles is often very different, predictions were performed on multiple supertypes to cover the polymorphic loci. NetMHC was used for the prediction for 12 supertypes of MHC-I locus. A binding affinity threshold of 500 nM was used as the cutoff for MHC-I binding [26]. Both MHCPred 2.0 and RANKPEP were used for MHC-II binding predictions to obtain consensus MHC-II epitopes. For MHCPred prediction, 3 supertypes of MHC-II locus were used, with a final binding affinity cutoff of 60 nM for MHC-II binding to obtain approximately the top 5% of the binders that correspond to regions of synthetic peptides reported to induce T-cell immune responses in mice [28]. For RANKPEP prediction, 50 MHC-II locus types were used and the cutoff was set at 4% of top-scoring peptides with above default threshold scores as reported in Ref. [27]. Data from individual supertypes of MHC-I or -II loci were combined for the analysis of each peptide. To ensure better predictive accuracy, only consensus results above the cutoff of both MHCPred and RANKPEP were considered as MHC-II binders.

Analysis of Protein Structural Features

The structural features of dengue E proteins were analyzed using known structures in PDB for DENV2, 1OAN (dimer), 1OK8 (post-fusion trimer), and 1 OKE (protein in complex with n-octyl-b-D-glucoside) [8, 29], and the DENV3 structure, 1UZG (dimer) [12]. The extent of exposure of amino acid residues was determined by computing the relative accessible surface area (ASA) using the POLYVIEW server [30]. Relative ASA of a residue is the ratio of the ASA of that residue in the protein to ASA of the same residue in the fully extended tripeptide alanine-residue-alanine. Based on the value of the relative ASA, the residues were grouped as buried (0.0-0.60) or exposed (0.61-1.0). To determine interactions across the dimer and trimer interface, the occluded surface (OS) area was computed using the method of Pattabiraman et al. [31]. Residues with OS area >0.5 Å$^2$ were considered as interacting. The conformational rearrangements occurring during the dimer to trimer transition were measured by the changes in the backbone torsion angles u and w between the DENV2 E protein dimer (1OAN) and trimer (1OK8). The conformational angles were obtained using the DSSP program [32], and the difference in the backbone torsion angles, Du and Dw, for each amino acid residue was calculated.

Results

Sequence Conservation of E Proteins in the Flavivirus Genus

Sequence conservation of E proteins among dengue species and other members of the genus Flavivirus was studied based on structure-guided multiple sequence alignment using 12 representative sequences chosen from the major flavivirus groups where the genome polyproteins are available. The multiple sequence alignment shows 72 completely conserved amino acid residues in the 12 flaviviruses [65 including FIG. 1]. These residues include cysteines forming the six pairs of disulfide-bonds [33] that stabilize loop structures in the three structural domains of E protein. Other crucial structure-stabilizing interactions by the flavivirus-conserved amino acids include the D98-K110 salt bridge, several intramolecular hydrogen bonds involving D10, C30, G100, W101, C105, L216, and L218, and the hydrophobic environment provided by leucines (L216, L218, and L264) and V208. Also, completely conserved among flaviviruses are two pairs of residues involved in interactions of domains I and III, R9 and E368, which form a salt bridge, and H144 and H317 that are involved in hydrogen bonds with the main chain of the opposite domain across the interface [34].

The most highly conserved region in flavivirus E protein is 98DRGWGNGCGLFGKG111, where 13 of the 14 residues are strictly conserved [65 including FIG. 1]. This peptide, contained in an internal loop between two b strands on domain DII, corresponds to the known fusion motif [8] involved in DENV infectivity. The highly variable region 380IGVEPGQLKL389, in the lateral loop on domain III, has been implicated in receptor-binding of DENV2 [35] and tick-borne viruses [34].

Sequence Conservation of E Proteins in the Dengue Species

The alignment of representative E protein sequences of the four dengue serotypes reveals a very high degree of sequence conservation as expected due to their close evolutionary relationship [65 including FIG. 2]. This alignment identified negatively selected sites in each serotype and sites under negative selection pressure only in a specific serotype and not in a merged dataset. A total of 260 residues (~53% of all residues) are conserved in the multiple alignment of the four sequences. The conservation spans across the entire sequence length, including complete sequence identity of the fusion motif in D98-G111 and the two known N-linked glycosylation sites at N67 and N153 [9] with the Asn-X-Thr/Ser-X potential glycosylation site motif (X can be any residue except for proline) [65 including FIG. 2].

Shannon entropy was used to quantify the conservation of each amino acid position in the multiple sequence alignment of 740 E proteins from all four serotypes. The entropy ranges from 0.365 to 2.42 bits, with scores <0.6 for highly conserved residues, 0.6-0.9 for conservative amino acid substitutions, and >0.9 for nonconserved residues. The mean entropy of the full-length protein is 0.539 bits, and 55 and 91% of the positions have entropies of <0.6 and <0.9, respectively [65 including FIG. 2].

Comparisons of the entropy measure of the three structural domains DI (amino acids 1-52, 134-191, 280-295), DII (aa 53-133, 192-279) and DIII (aa 296-394), and the C-terminal region (aa 394-495) reveal regions of different sequence variability. In particular, domain DIII has the highest variability, with an entropy mean of 0.703 bits and entropies of <0.6 and <0.9 for 44 and 86% of the positions. Interestingly, serotype-specific neutralization escape mutant sites in DENV E proteins are all located on the surface of domain III [12]. Twelve sequence regions are highly conserved in DENV E proteins, containing five or more consecutive amino acid sites with entropy scores of <0.6, namely, N8-G14, V24-D42, R73-E79, V97 S102, D192-M196, V208-W220, V252-H261, G281-C285, E314-T319, E370-G374, K394-G399, and R411-5424, designated as sequence regions I to XII, respectively [65 including FIG. 2].

Amino Acid Sites Under Selection Pressure in Dengue E Proteins

Estimates of synonymous or silent (dS) and non-synonymous or amino-acid altering (dN) nucleotide substitution rates at a given position in a codon alignment have become a standard measure of selective pressure, especially in the framework of maximum likelihood phylogenetic methods [22]. If dS is estimated to be significantly more than dN at a given site, (a dN/dS value of <1), this can be taken as evidence of purifying (negative) selective pressure on that site. That is, for that particular site amino acid changes are, on average, deleterious (negative selection). When the opposite is true, i.e. dN>dS, (dN/dS>1) there is selective pressure to generate and possibly maintain amino-acid polymorphisms, i.e. undergo adaptive change (positive selection). This unusual condition may reflect a change in the function of a gene or an immediate change in environmental conditions (such as a pathogen's response to an administered drug) that forces the organism to adapt.

To quantify selective pressure, dS and dN were estimated for each site of the alignment of individual dengue serotypes and also for all serotypes combined. The Tamura Nei (TN93) [36] model of nucleotide substitution bias (out of 203 possible models) was selected for all alignments. To each alignment we fitted one of four models of site-to-site rate variation (Constant: dS=dN=1; Proportional: dN is proportional to dS, which varies among sites; Non-synonymous: dS=1, dN varies among sites; and Dual: dS and dN vary among sites independently). Strong evidence supporting the Dual model of rate variation was observed in each alignment (shown in supplementary Table S1). This finding suggests that both dS and dN vary across sites, but there is no simple correlation pattern between the two rates [37].

Ninety negatively selected sites were identified in DENV1, 161 in DENV2, 49 in DENV3, and 57 in DENV4, while 186 sites were found to be under negative selection pressure in the large combined set with all four serotypes [65 including FIG. 2]. Because the signature of negative selection is the relative abundance of synonymous substitutions likely due to functional constraints, most negatively selected sites were shown to correspond to conserved residues or substitution of an amino acid by another with similar chemical properties (conservative substitutions). Altogether it was demonstrated that 138 out of 186 (74%) negative sites in the merged set have low entropy scores of <0.6 bits. Furthermore, 14 sites (C3, C60, R73, T189, F213, A267, F306, T319, S376, F392, K394, S424, G445, and V485) are negatively selected in at least three of the four serotypes as well as in the merged dataset (underlined residues); most are highly conserved and a few have conservative substitutions. Only 6 out of 186 (3%) negative sites in the merged set were identified as having >0.9 bits entropy scores (S95, P143, T180, S300, V309, and Y488). Note that while these sites are not conserved within the dengue species, they all correspond to negatively selected sites in one or two specific serotypes, possibly reflective of selective sweeps that have become fixed in individual serotypes and are now maintained by purifying selection (negative selection). Finally, several serotype specific negatively selected sites were also identified (19 in DENV1, 48 in DENV2, 7 in DENV3, 16 in DENV4). Most notable are the 5 (E383 and Q386-L389) DENV2 specific negative sites in the receptor-binding region [65 including FIG. 2].

Although there are several reports on the role of positively selected sites in pathogen-host interaction, such as evading host immunity [38-42], there are few reports of experimental validation of the functional significance of negatively selected sites. It has been shown that epitopes consisting of negatively selected sites perform better as vaccines than ones containing positively selected sites [43, 44]. The underlying assumption is that because negatively selected sites are less likely to change, due to functional constraints, vaccines or diagnostic targets directed against them may be more effective.

No extant positively selected sites were detected in any of the dengue serotypes in this study. Our findings agree with previous selection studies where constant dS across all sites was assumed a priori and the data were not stratified based on genotypes and passage types [45, 46]. Comparable analysis of E gene sequences from other flaviviruses, such as St. Louis encephalitis virus, West Nile virus and Yellow fever virus, also did not detect any positive selection [47]. In order to screen for possible selection on amino-acid residues prior to the divergence of serotypes, we estimated dN and dS along the four tree branches separating individual serotype clades in the joint phylogeny using a fixed effects likelihood method [22]. Five sites with evidence of ancient positive selection were suggested (P £ 0.001): N83, P132, E174, Q293, and L458.

MHC Peptide Binding in Dengue E Proteins

MHC-I peptide binding prediction using NetMHC [25] identified several potential binding regions for each of the four E proteins. However, the overall MHC-I binding affinity was low and the number of high binders was small. Low predicted MHC-I binding was further confirmed using MHCPred (data not shown). These results are consistent with the observation that E proteins mainly induce antibody response to DENV, while non structural protein 3 (NS3) mainly induces T-cell immune responses to DENV [48].

Many MHC-II binding peptides (Th-cell epitopes) were predicted by both MHCPred and RANKPEP [27] above the affinity threshold (56, 64, 50, and 53 peptides for DENV1, DENV2, DENV3, and DENV4, respectively, had affinities ranging from 1 to 60 nM) [65 including FIG. 2]. Of these, 11 peptides have been identified in regions common to all four serotypes and represent immunogenic consensus sequence epitopes in the DENV species. High-affinity MHC-II binding peptides among the top-ranking predictions have been identified that are unique to one of the four serotypes. The predicted binding peptides common to all serotypes generally are present in more conserved regions with low-entropy and/or negatively selected sites, except the last two consensus binding peptides occurring in the C-terminal transmembrane region. On the other hand, most predicted serotype-specific binding peptides are in variable regions with lower sequence conservation. Interestingly, the most highly variable domain DIII contains only predicted serotype-specific binding peptides, but no consensus binding peptides common to all four serotypes [65, including FIG. 2].

To cross-validate the predicted results, we further mapped the 64 predicted MHC-II binders of DENV2 E protein to regions covered by synthetic peptides that were previously determined to mimic Th-cell epitopes and to elicit antibody responses in three different mouse strains [28] (amino acid regions of peptides in Supplementary Table S2). As 15 of the predicted peptides are not completely covered within regions of the synthetic peptides, the comparison was based on the remaining 49 predicted peptides. We noted that 39 of the 49 (80% true positive) predicted MHC-II peptides were matched with 16 synthetic peptides that experimentally tested positive for Th-cell epitopes; while the remaining 10 binders (20% false positive) correlated to synthetic peptides that did not elicit an immune response either in vitro or in vivo [28]. Conversely, the computational methods predicted all but one of the 17 synthetic peptides shown to induce an immune response (Table S2), yielding a 94% (16/17) recall rate. The predictive accuracy observed here is consistent with the benchmarking results of epitope prediction programs [49].

Consistent with the notion that the variable surface residues are likely to be responsible for the serotype-specific immunogenic variation, we identified four specific sequence regions (329DGS331, 342LEKRH346, 360EKDS363, and 383EPG385) that also match with predicted serotype specific Th-cell epitopes and/or neutralizing mAB-binding regions and experimentally determined Th-cell epitopes [28]. These serotype-specific Th-cell binders, coupled with the predicted consensus Th-cell binders, reveal dengue immunogenic properties at both the species and serotype levels [65 including FIG. 2].

Structural Features of Dengue E Proteins

Several structural computational analyses were used to assign functional roles to amino acid residues in dengue E proteins [65 including FIG. 3]. Based on the relative accessible surface area (ASA), buried residues that are important to maintain the structural integrity of the protein and exposed residues that may provide clues about protein interaction and immunogenicity were identified. The dimmer (pre-fusion) and trimer (post-fusion) structures of DENV2 E protein each have about 60 exposed residues (relativeASA>0.6), half of which remain exposed on both the dimmer and the trimer surfaces.

The solved structures for DENV2 and DENV3 show that there are minor structural differences at the viral surface of the two serotypes. It has been suggested that the noncon-served residues exposed on the viral protein surface may be involved in differential antibody binding [12]. Among 43 non-conserved residues across the four serotypes (entropy>0.9 bits), 19 are exposed on the surface of either oligomer, including 5 in the dimer only (K157, P243, Q293, E343, and E360), 1 in the trimer only (L342), and 13 in both the dimer and trimer (N83, K88, K122, E174, D203, Q227, S274, S300, D329, R345, H346, D362, and G385). Domain III alone has 9 exposed and non-conserved residues, including 6 exposed in both the dimer and trimer.

A total of 128 interface residues critical for dimerization and trimerization based on the occluded surface area were identified. In particular, it was noted that several residues in the fusion motif, D98, L107, F108, and K110, are involved in interactions at both the dimer and trimer interfaces of DENV2 E proteins, as well as the dimer interface of DENV3 E protein (not shown). It was further noted that most of these interface residues are highly conserved within the dengue species. Approximately 73% (94 residues) of all interface residues either have entropy scores <0.6 or are negatively selected, and only 4% (5 residues) are non-conserved with entropy scores >0.9. A few [18] interface residues are among the completely conserved residues in all 12 flaviviruses. The interface residues represent potential candidates for mutation experiments that may alter oligomerization. This region may also be a potential target for inhibitors that prevent oligomerization [65 including FIG. 3].

There are significant conformational rearrangements in the main chain during the dimer to trimer transition. The plot of the difference in the backbone torsion angles (Du and Dw) shows several regions with major conformational changes, such as 1-19,242-246, 289-298, and 343-350. Many residues change from buried to exposed during the transition, suggesting the importance of these residues in the fusion mechanism. For example, buried residues M1, H244, K246, G254, G330, and K344 in the dimmer become exposed in the trimer after significant conformational changes in the main chain, while residues including S16, Q52, Q167, S169, P243, D290, Q293, S331, and E343 change from exposed to buried during trimerization [65 including FIG. 3].

Comparative Analysis of Computational and Experimental Data

To estimate the relative accuracy of our analyses, computational data on sequence conservation, negative selection, structural features, and T-cell epitopes were compared with each other and also with published, experimentally determined functional sites [65 including FIG. 4]. Such integrated analysis allowed identification of sites that are exposed in the dimer and are also negatively selected (e.g. N37, N67, K88, E195, P217, G266, D290, S300, D362, F373, and E383). Other sites were identified, such as 266GAT268 and 445GAAFS449, which (a) belong to the group of three or more consecutive sites under negative selection pressure in DENV2, (b) have a residue that is negatively selected in at least three of the serotypes (as observed in the merged dataset), and (c) are also part of a predicted epitope. Overall, our computational results are in agreement with experimental information (see supplementary Table S3). The high affinity MHC-II binding peptides predicted here correlated to 80% of the synthetic peptides shown experimentally to induce T-cell immune responses [28]. The correlation between computationally predicted data and available experimental information suggests that the computational approaches used here relate rather well to biological features.

Identification of Functionally Significant Sites

Development of diagnostics with low rates of false negatives and of vaccines difficult to circumvent (by nature or by man) would benefit by identifying the amino acid sites that should remain unaltered in spite of natural changes or artificial modification of dengue virus. We integrated all the computational results described above in this study and searched for sites in E protein that were (a) conserved, (b) consensus T-cell epitopes, and (c) exposed. A site-by-site analysis of the sequence of E protein revealed, as expected, that different features were distributed throughout the sequence. Rather unexpectedly, however, we observed six sites that had more than one feature in a confined region of E protein. The sites having several features might be of particular importance to the viral genome and, therefore, unlikely to change without profound effects on infectivity and/or virus propagation. We considered these six singular sites (N37, Q211, D215, P217, H244, K246) as potential candidate regions of the E protein for diagnostics and vaccine development. It was noted that 2 sites (N37, P217) are exposed in both dimer and trimer, 2 sites (Q211, D215) are exposed only in the dimer, and 2 sites (H244, K246) are exposed only in the trimer. Out of these six sites, H244 and K246 undergo conformational change between dimer and trimer forms [65 including FIG. 4]. Peptides for creating diagnostics and vaccines against Dengue virus (any subtype) include: SEQ ID NO: 1: MAKNKPTLD; SEQ ID NO: 2: KLTNTTT; SEQ ID NO 3: GLDFNEM; SEQ ID NO: 4: WLVHRQWFLDLPLPW; SEQ ID NO: 5: FKNPHAKKQ; SEQ ID NO: 6: ALTGATEIQ; SEQ ID NO: 7: IMDLEKRHVL; SEQ ID NO: 8: GVEPGQLK; SEQ ID NO: 9: GAAFSGVSW; and SEQ ID NO: 10: VGIVTLYL. Peptides for creating diagnostics and vaccines against Yellow fever virus include: SEQ ID NO: 11: WIVDRQWAQDLTLPW and SEQ ID NO: 12: FEPPHAATI. Peptides for creating diagnostics and vaccines against West Nile include SEQ ID NO: 13: FLVHREWFMDLNLPW and SEQ ID NO: 14: FEEPHATKQ. Peptides to create diagnostics and vaccines against Tick Borne Encephalitis virus include: SEQ ID NO: 15: WQVHRDWFNDLALPW and SEQ ID NO: 16: FGAPHAVKM.

Discussion

In this study, the sequence alignment of the flavivirus E proteins and the entropy measure and negative selection results for dengue E proteins have allowed us to identify sites and regions that are conserved across the flavivirus genus or within the dengue species, as well as variable regions that reflect serotype specific functional constraints. Such analyses of conserved sites at the different taxonomic levels allow us to differentiate residues of general importance to the infectivity of flaviviruses from residues that may be specific to the dengue viruses. For example, among the 12 dengue-conserved sequence regions, regions I-IV and VI-VIII are also highly conserved in other flaviviruses, encompassing over half of the 72 completely conserved residues in flavivirus E proteins [65 including FIG. 4]. These regions also cover 16 of the 18 DENV2 dimer or trimer interface residues that are completely conserved in all 12 flaviviruses. On the other hand, sequence region V (D192-M196) is dengue species specific. Interestingly, region V overlaps with a 13-amino acid sequence region that contains 11 negatively selected sites identified to be under functional constraints. Such selection pressure analysis of codon-based DNA alignments is ideal for identifying functionally important residues in serotypes that may not be reflected in the amino acid alignments at the species and serotype level [50].

Several dengue-specific sites were identified. For example, while the N153 glycosylation site is conserved in several flaviviruses, the N67 site is unique to DENV. It appears that dengue viruses are heterogeneous in their use of the glycosylation sites [51] and the precise function of the second glycosylation site is still under investigation [52]. The significance of this site is not known, although it has been noted that the loss of the N67 glycosylation site may result in a higher pH threshold for conformational change [53]. We have identified variable residues exposed on the surface of the E protein that are likely to be responsible for the immunogenic variation among dengue serotypes. Especially notable is the sequence region 342LEKRH346 in structural domain III, which consists of five surface exposed residues (1 in dimer, 2 in trimer and 2 in both dimer and trimer) in the beginning of a region (aa 343-350) that undergoes major conformational changes during the dimer to trimer transition, with E343 becoming buried and K344 becoming exposed. Four (L342, E343, R345, H346) of the five residues are not conserved among the serotypes and have entropy scores >0.9. Another variable and exposed region is within the 10-aa receptor-binding region (1380-L389) that contains 4 exposed residues, including the 383EPG385 triad critical for mAB binding [12].

Recent progress in molecular-based vaccine strategies, such as recombinant subunit dengue vaccines, has provided hope for the control of the disease [6]. The phenomenon of antibody dependent enhancement of dengue disease has spurred attempts to develop a tetravalent dengue vaccine that produces neutralizing antibodies against all four serotypes [54]. Large-scale analysis of antigenic diversity of T-cell epitopes for dengue virus [55] indicates that there are limited numbers of antigenic combinations in E protein sequence variants, and that short regions of the protein are sufficient to capture the antigenic diversity of T-cell epitopes. Taken together, the 11 predicted consensus Th-cell epitopes that we identified, especially the 3 epitopes containing the 6 select target sites, are of special interest as potential candidate regions for inclusion in developing epitope-driven vaccines against dengue viruses. A T-cell epitope-driven vaccine design approach has been used for HIV-1 (e.g. the GAIA vaccine) [56] with promising results [57].

REFERENCES

1. M. H. van Regenmortel, M. A. Mayo, C. M. Fauquet, J. Maniloff, Arch. Virol. 145, 2227 2232 (2000)
2. J. R. Stephenson, Bull. World Health Organ. 83, 308-314 (2005)
3. G. N. Malavige, S. Fernando, D. J. Fernando, S. L. Seneviratne, Postgrad. Med. J. 80, 588-601 (2004)
4. J. T. Roehrig, R. A. Bolin, R. G. Kelly, Virology 246, 317-328 (1998)
5. K. C. Leitmeyer, D. W. Vaughn, D. M. Watts, R. Salas, I. Villalobos de Chacon, C. Ramos, R. Rico-Hesse, J Virol 73, 4738-4747 (1999)
6. U. C. Chaturvedi, R. Shrivastava, R. Nagar, Indian J. Med. Res. 121, 639-652 (2005)
7. E. Lee, R. A. Hall, M. Lobigs, J. Virol. 78, 8271-8280 (2004)
8. Y. Modis, S. Ogata, D. Clements, S. C. Harrison, Nature 427, 313-319 (2004)
9. T. P. Monath, J. Arroyo, I. Levenbook, Z. X. Zhang, J. Catalan, K. Draper, F. Guirakhoo, J. Virol. 76, 1932-1943 (2002)
10. E. Lee, R. C. Weir, L. Dalgarno, Virology 232, 281-290 (1997)
11. F. X. Heinz, S. L. Allison, Adv. Virus Res. 55, 231-269 (2000)
12. Y. Modis, S. Ogata, D. Clements, S. C. Harrison, J. Virol. 79, 1223-1231 (2005)

13. K. Hiramatsu, M. Tadano, R. Men, C. J. Lai, Virology 224, 437-445 (1996)
14. C. H. Wu, R. Apweiler, A. Bairoch, D. A. Natale, W. C. Barker, B. Boeckmann, S. Ferro, E. Gasteiger, H. Huang, R. Lopez, M. Magrane, M. J. Martin, R. Mazumder, C. O'Donovan, N. Redaschi, B. Suzek, Nucleic Acids Res. 34, D187-D191 (2006)
15. Y. Wang, L. Y. Geer, C. Chappey, J. A. Kans, S. H. Bryant, Trends Biochem. Sci. 25, 300-302 (2000)
16. N. Deshpande, K. J. Addess, W. F. Bluhm, J. C. Merino-Ott, W. Townsend-Merino, Q. Zhang, C. Knezevich, L. Xie, L. Chen, Z. Feng, R. K. Green, J. L. Flippen-Anderson, J. Westbrook, H. M. Berman, P. E. Bourne, Nucleic Acids Res. 33, D233-D237 (2005)
17. J. D. Thompson, D. G. Higgins, T. J. Gibson, Nucleic Acids Res. 22, 4673-4680 (1994)
18. K. Sjolander, K. Karplus, M. Brown, R. Hughey, A. Krogh, I. S. Mian, D. Haussler, Comput. Appl. Biosci. 12, 327-345 (1996) 19. D. L. Wheeler, T. Barrett, D. A. Benson, S. H. Bryant, K. Canese, D. M. Church, M. DiCuccio, R. Edgar, S. Federhen, W. Helmberg, D. L. Kenton, O. Khovayko, D. J. Lipman, T. L. Madden, D. R. Maglott, J. Ostell, J. U. Pontius, K. D. Pruitt, G. D. Schuler, L. M. Schriml, E. Sequeira, S. T. Sherry, K. Sirotkin, G. Starchenko, T. O. Suzek, R. Tatusov, T. A. Tatusova, L. Wagner, E. Yaschenko, Nucleic Acids Res. 33, D39-D45 (2005)
20. S. Kumar, K. Tamura, M. Nei, Brief Bioinform. 5, 150-163 (2004)
21. S. L. Kosakovsky Pond, S. D. Frost, S. V. Muse, Bioinformatics 21, 676-679 (2005)
22. S. L. Kosakovsky Pond, S. D. Frost, Mol. Biol. Evol. 22, 1208-1222 (2005)
23. S. L. Kosakovsky Pond, S. V. Muse, in HyPhy: Hypothesis Testing Using Phylogenies in Statistical Methods in Molecular Evolution ed. by R. Nielsen (Springer, N.Y., 2005), pp. 125-182
24. S. L. Kosakovsky Pond, D. Posada, M. B. Gravenor, C. H. Woelk, S. D. Frost, Mol. Biol. Evol. 23, 1891-1901 (2006)
25. M. Nielsen, C. Lundegaard, P. Worning, C. S. Hvid, K. Lamberth, S. Buus, S. Brunak, O. Lund, Bioinformatics 20, 1388-1397 (2004)
26. P. Guan, I. A. Doytchinova, C. Zygouri, D. R. Flower, Nucleic Acids Res. 31, 3621-3624 (2003)
27. P. A. Reche, J. P. Glutting, H. Zhang, E. L. Reinherz, Immunogenetics 56, 405-419 (2004)
28. J. T. Roehrig, P. A. Risi, J. R. Brubaker, A. R. Hunt, B. J. Beaty, D. W. Trent, J. H. Mathews, Virology 198, 31-38 (1994)
29. Y. Modis, S. Ogata, D. Clements, S. C. Harrison, Proc. Natl. Acad. Sci. USA 100, 6986-6991 (2003)
30. A. A. Porollo, R. Adamczak, J. Meller, Bioinformatics 20, 2460-2462 (2004)
31. N. Pattabiraman, K. B. Ward, P. J. Fleming, J. Mol. Recognit. 8, 334-344 (1995)
32. W. Kabsch, C. Sander, Biopolymers 22, 2577-2637 (1983)
33. T. Nowak, G. Wengler, Virology 156, 127-137 (1987)
34. S. Bressanelli, K. Stiasny, S. L. Allison, E. A. Stura, S. Duquerroy, J. Lescar, F. X. Heinz, F. A. Rey, EMBO J. 23, 728-738 (2004)
35. J. J. Hung, M. T. Hsieh, M. J. Young, C. L. Kao, C. C. King, W. Chang, J. Virol. 78, 378-388 (2004)
36. K. Tamura, M. Nei, Mol. Biol. Evol. 10, 512-526 (1993)
37. S. L. Kosakovsky Pond, S. V. Muse, Mol. Biol. Evol. 22(12):2375-2385 (2005)
38. G. Blanc, M. Ngwamidiba, H. Ogata, P. E. Fournier, J. M. Clayerie, D. Raoult, Mol. Biol. Evol. 22, 2073-2083 (2005)
39. M. Anisimova, Z. Yang, J. Mol. Evol. 59, 815-826 (2004)
40. A. J. Leslie, K. J. Pfafferott, P. Chetty, R. Draenert, M. M. Addo, M. Feeney, Y. Tang, E. C. Holmes, T. Allen, J. G. Prado, M. Altfeld, C. Brander, C. Dixon, D. Ramduth, P. Jeena, S. A. Thomas, A. St John, T. A. Roach, B. Kupfer, G. Luzzi, A. Edwards, G. Taylor, H. Lyall, G. Tudor-Williams, V. Novelli, J. Martinez-Picado, P. Kiepiela, B. D. Walker, P. J. Goulder, Nat. Med. 10, 282-289 (2004)
41. Y. Suzuki, T. Gojobori, Mol. Biol. Evol. 16, 1315-1328 (1999)
42. Y. Suzuki, T. Gojobori, Gene 276, 83-87 (2001)
43. Y. Suzuki, Gene 328, 127-133 (2004)
44. Y. Suzuki, Mol. Biol. Evol. 23, 1902-1911 (2006)
45. S. S. Twiddy, C. H. Woelk, E. C. Holmes, J. Gen. Virol. 83, 1679-1689 (2002)
46. C. Klungthong, C. Zhang, M. P. Mammen Jr., S. Ubol, E. C. Holmes, Virology 329, 168-179 (2004)
47. Z. Yang, J. P. Bielawski, Trends Ecol. Evol. 15, 496-503 (2000)
48. A. L. Rothman, J. Clin. Invest. 113, 946-951 (2004)
49. P. Guan, C. K. Hattotuwagama, I. A. Doytchinova, D. R. Flower, Appl. Bioinform. 5, 55-61 (2006)
50. N. Goldman, Z. Yang, Mol. Biol. Evol. 11, 725-736 (1994)
51. A. J. Johnson, F. Guirakhoo, J. T. Roehrig, Virology 203, 241-249 (1994)
52. C. W. Davis, L. M. Mattei, H. Y. Nguyen, C. Ansarah-Sobrinho, R. W. Doms, T. C. Pierson, J. Biol. Chem. 281, 37183-37194 (2006)
53. F. Guirakhoo, A. R. Hunt, J. G. Lewis, J. T. Roehrig, Virology 194, 219-223 (1993)
54. D. H. Holman, D. Wang, K. Raviprakash, N. U. Raja, M. Luo, J. Zhang, K. R. Porter, J. Y. Dong, Clin. Vaccine Immunol. 14, 182-189 (2007)
55. A. M. Khan, A. Heiny, K. X. Lee, K. Srinivasan, T. W. Tan, J. T. August, V. Brusic, BMC Bioinform. 7(Suppl 5), S4 (2006)
56. A. S. De Groot, E. A. Bishop, B. Khan, M. Lally, L. Marcon, J. Franco, K. H. Mayer, C. C. Carpenter, W. Martin, Methods 34, 476-487 (2004)
57. O. A. Koita, D. Dabitao, I. Mahamadou, M. Tall, S. Dao, A. Tounkara, H. Guiteye, C. Noumsi, O. Thiero, M. Kone, D. Rivera, J. A. McMurry, W. Martin, A. S. De Groot, Hum. Vaccin. 2, 119-128 (2006)
58. C. L. Kao, C. C. King, D. Y. Chao, H. L. Wu, G. J. Chang, J. Microbiol. Immunol. Infect. 38, 5-16 (2005)
59. Sambrook et al., Molecular Cloning: A Laboratory Manual, 2.sup.nd Ed., Cold Spring Harbor Laboratory Press, Plainview, N.Y., 1989
60. Harlow and Lane, Antibodies: A laboratory Manual, 1988, Cold Springs Harbor Laboratory Press
61 Kohler and Milstein, (1975) Nature (London) 256, 495 497
62. Kennet, R., (1980) in Monoclonal Antibodies Kennet et al., Eds. pp. 365 367, Plenum Press, NY
63. Tsarev et al., 1993a; Tsarev et al., 1994a
64. Amon, R. (Ed.) Synthetic Vaccines I:83 92, CRC Press, Inc., Boca Raton, Fla., 1987
65. R. Mazumder, Z.-Z. Hu, C. R. Vinayaka, J.-L. Sagripanti, S. D. W. Frost, S. L. K. Pond, C. H. Wu., "Computational Analysis and Identification of Amino Acid Site in Dengue E Proteins Relevant to Development of Diagnostics and Vaccines," Virus Genes, Springer Science-Business Media, LLC 2007

The foregoing description of embodiments of the present invention provides an exemplary illustration and description, but is not intended to be exhaustive or to limit the invention to the precise form disclosed. Modifications and variations are possible in light of the above teachings or may be acquired from practice of the invention.

What is claimed is:

1. A purified and isolated peptide consisting of a peptide selected from the group of amino acid sequences consisting of SEQ ID NO: 11, SEQ ID NO: 13, and SEQ ID NO: 15.

2. An isolated and purified recombinant fusion protein consisting of a Flaviviral peptide consisting of an amino acid sequence selected from the group consisting of SEQ ID NO: 11, SEQ ID NO: 12, and SEQ ID NO: 15; and a heterologous amino acid sequence fused to said peptide.

3. The recombinant fusion protein according to claim 2, wherein the beterologous amino acid sequence codes for glutathione S-transferase.

4. The purified and isolated peptide of claim 1, wherein said peptide is contained in a liquid saline solution including an adjuvant to produce a composition for stimulating an immune response when administered to an individual.

5. A diagnostic test kit for the detection of antibodies to a flavivirus, comprising: one or more purified and isolated peptide(s) consisting of one or more peptides selected from the group of amino acid sequences consisting of SEQ ID NO: 11, SEQ ID NO: 13, and SEQ ID NO: 15; and an indicator reagent capable of detecting an immunological (antigen-antibody) complex which contains said isolated peptide.

6. The diagnostic test kit according to claim 5, which further comprises one or more control standards and a specimen diluent and/or washing buffer.

7. The diagnostic test kit according to claim 5, wherein said isolated peptide(s) is immobilized to a solid support.

8. The diagnostic test kit according to claim 7, wherein the solid support is a titration microplate well.

* * * * *

SEQUENCE LISTING

```
<160> NUMBER OF SEQ ID NOS: 16

<210> SEQ ID NO 1
<211> LENGTH: 9
<212> TYPE: PRT
<213> ORGANISM: Dengue virus

<400> SEQUENCE: 1

Met Ala Lys Asn Lys Pro Thr Leu Asp
1               5

<210> SEQ ID NO 2
<211> LENGTH: 7
<212> TYPE: PRT
<213> ORGANISM: Dengue virus

<400> SEQUENCE: 2

Lys Leu Thr Asn Thr Thr Thr
1               5

<210> SEQ ID NO 3
<211> LENGTH: 7
<212> TYPE: PRT
<213> ORGANISM: Dengue virus

<400> SEQUENCE: 3

Gly Leu Asp Phe Asn Glu Met
1               5

<210> SEQ ID NO 4
<211> LENGTH: 15
<212> TYPE: PRT
<213> ORGANISM: Dengue virus

<400> SEQUENCE: 4

Trp Leu Val His Arg Gln Trp Phe Leu Asp Leu Pro Leu Pro Trp
1               5                   10                  15

<210> SEQ ID NO 5
<211> LENGTH: 9
<212> TYPE: PRT
<213> ORGANISM: Dengue virus

<400> SEQUENCE: 5

Phe Lys Asn Pro His Ala Lys Lys Gln
1               5

<210> SEQ ID NO 6
<211> LENGTH: 9
<212> TYPE: PRT
<213> ORGANISM: Dengue virus

<400> SEQUENCE: 6

Ala Leu Thr Gly Ala Thr Glu Ile Gln
1               5

<210> SEQ ID NO 7
<211> LENGTH: 10
<212> TYPE: PRT
<213> ORGANISM: Dengue virus
```

```
<400> SEQUENCE: 7

Ile Met Asp Leu Glu Lys Arg His Val Leu
1               5                   10

<210> SEQ ID NO 8
<211> LENGTH: 8
<212> TYPE: PRT
<213> ORGANISM: Dengue virus

<400> SEQUENCE: 8

Gly Val Glu Pro Gly Gln Leu Lys
1               5

<210> SEQ ID NO 9
<211> LENGTH: 9
<212> TYPE: PRT
<213> ORGANISM: Dengue virus

<400> SEQUENCE: 9

Gly Ala Ala Phe Ser Gly Val Ser Trp
1               5

<210> SEQ ID NO 10
<211> LENGTH: 8
<212> TYPE: PRT
<213> ORGANISM: Dengue virus

<400> SEQUENCE: 10

Val Gly Ile Val Thr Leu Tyr Leu
1               5

<210> SEQ ID NO 11
<211> LENGTH: 15
<212> TYPE: PRT
<213> ORGANISM: Yellow fever virus

<400> SEQUENCE: 11

Trp Ile Val Asp Arg Gln Trp Ala Gln Asp Leu Thr Leu Pro Trp
1               5                   10                  15

<210> SEQ ID NO 12
<211> LENGTH: 9
<212> TYPE: PRT
<213> ORGANISM: Yellow fever virus

<400> SEQUENCE: 12

Phe Glu Pro Pro His Ala Ala Thr Ile
1               5

<210> SEQ ID NO 13
<211> LENGTH: 15
<212> TYPE: PRT
<213> ORGANISM: West nile virus

<400> SEQUENCE: 13

Phe Leu Val His Arg Glu Trp Phe Met Asp Leu Asn Leu Pro Trp
1               5                   10                  15

<210> SEQ ID NO 14
<211> LENGTH: 9
<212> TYPE: PRT
<213> ORGANISM: West nile virus

<400> SEQUENCE: 14
```

```
Phe Glu Glu Pro His Ala Thr Lys Gln
1               5

<210> SEQ ID NO 15
<211> LENGTH: 15
<212> TYPE: PRT
<213> ORGANISM: Tick borne encephalitis virus

<400> SEQUENCE: 15

Trp Gln Val His Arg Asp Trp Phe Asn Asp Leu Ala Leu Pro Trp
1               5                   10                  15

<210> SEQ ID NO 16
<211> LENGTH: 9
<212> TYPE: PRT
<213> ORGANISM: Tick borne encephalitis virus

<400> SEQUENCE: 16

Phe Gly Ala Pro His Ala Val Lys Met
1               5
```